(12) United States Patent
Busch (10) Patent No.: US 11,937,773 B2
(45) Date of Patent: Mar. 26, 2024

(54) ENDOSCOPE WITH A SUCTION VALVE HAVING A SEALING BUTTON

(71) Applicant: AMBU A/S, Ballerup (DK)

(72) Inventor: David Busch, Weyarn (DE)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 17/453,398

(22) Filed: Nov. 3, 2021

(65) Prior Publication Data
US 2022/0133131 A1 May 5, 2022

(30) Foreign Application Priority Data

Nov. 5, 2020 (DE) .......................... 102020129208.2

(51) Int. Cl.
*A61B 1/00* (2006.01)
*A61B 1/015* (2006.01)
*A61B 1/05* (2006.01)

(52) U.S. Cl.
CPC ...... *A61B 1/00068* (2013.01); *A61B 1/00045* (2013.01); *A61B 1/015* (2013.01); *A61B 1/05* (2013.01)

(58) Field of Classification Search
CPC ............ A61B 1/00009; A61B 1/00068; A61B 1/00094; A61B 1/00119; A61B 1/015; A61B 1/05
See application file for complete search history.

(56) References Cited

U.S. PATENT DOCUMENTS

| | | | |
|---|---|---|---|
| 5,840,015 A | 11/1998 | Ogino | |
| 5,871,441 A * | 2/1999 | Ishiguro | ................ A61B 1/122 |
| | | | 600/159 |
| 6,849,043 B2 | 2/2005 | Kondo | |
| 6,908,429 B2 | 6/2005 | Heimberger | |

(Continued)

FOREIGN PATENT DOCUMENTS

| | | | |
|---|---|---|---|
| JP | 2004135890 A | * | 5/2004 |
| JP | 2012065767 A | | 4/2012 |
| JP | 2012071023 A | | 4/2012 |

OTHER PUBLICATIONS

Search report and English translation from German patent application No. 10 2020 129 208.2, dated Aug. 2, 2021, 14 pgs.

*Primary Examiner* — John P Leubecker
*Assistant Examiner* — Jae Woo
(74) *Attorney, Agent, or Firm* — Faegre Drinker Biddle & Reath LLP (57) ABSTRACT

An endoscope including: a handle, a distal tip unit, an endoscope shaft connecting the handle and the distal tip unit, a working channel provided in the endoscope shaft, and a suction valve configured to control a suction through the working channel and having a valve closed state and a valve open state. The suction valve includes a housing having an inlet opening connected to the working channel and an outlet opening; and a piston unit inserted in the housing. The piston unit comprises a movable piston, a button attached to the piston, a fixation ring arranged stationary in the housing and a spring arranged and acting between the fixation ring and the button or piston. The button is a one-piece or integral part having an integrated sealing portion contacting the housing and providing a sealing between the button and the housing in the valve open state.

17 Claims, 4 Drawing Sheets

(56) References Cited

U.S. PATENT DOCUMENTS

| | | |
|---|---|---|
| 9,585,545 B2 | 3/2017 | Anderson et al. |
| 10,898,062 B2 | 1/2021 | Wolfe |
| 2011/0208003 A1* | 8/2011 | Yamane .................. A61B 1/12 |
| | | 600/159 |
| 2012/0071844 A1* | 3/2012 | Yamane ............. A61B 1/00068 |
| | | 604/319 |
| 2013/0338442 A1* | 12/2013 | Anderson .......... A61B 1/00094 |
| | | 600/154 |
| 2017/0290495 A1* | 10/2017 | Ando ................ A61B 1/00068 |

* cited by examiner

ENDOSCOPE WITH A SUCTION VALVE HAVING A SEALING BUTTON

CROSS-REFERENCE TO RELATED APPLICATIONS

This application claims priority from and the benefit of German Patent Application No. DE 10 2020 129 208.2, filed Nov. 5, 2020, which is incorporated herein by reference in its entirety.

TECHNICAL FIELD

The present disclosure relates to an endoscope, and more particularly, to an endoscope with a suction valve configured to control suction through a working channel of the endoscope.

BACKGROUND

Endoscopes and similar specialized instruments such as bronchoscopes, arthroscopes, colonoscopes, laparoscopes and duodenoscopes are well known from the state of the art and are used for visual examination and diagnosis of hollow organs and body cavities, as well as to assist in surgery, e.g. for a targeted tissue sampling. Basically, a distal tip unit of an endoscope, which is connected to an endoscope handle via an endoscope shaft, can be inserted into a hollow organ or body cavity to be investigated with the endoscope. Both reusable and disposable endoscopes are known from the state of the art.

When examining an object such as a body cavity or hollow organ with an endoscope it is desirable to have a clear view/visibility of the examined object. However, the visibility of such an object is often affected by mucus or other undesirable fluid content. It is thus desirable to remove such mucus or undesirable fluid content using a suction device, such as a vacuum pump. In order to connect the suction device to the endoscope and to control a suction that shall be applied to the examined object, it is basically known to use/provide a suction valve.

For example, a suction valve for an endoscope may be connected to a working channel of the endoscope and may be configured to allow or prevent a suction/suction effect in the working channel. When the suction valve is in a valve closed position (i.e. a closed position of the suction valve), a fluid/air flow through the working channel is blocked by the suction valve. When suction is desired in the working channel, an operator/a user can (manually) operate the suction valve (e.g. by depressing a button of the valve) in order to bring the suction valve in a valve open position (i.e. an open position of the suction valve). In the open position of the suction valve a flow channel inside the suction valve connects the working channel to the suction device. In particular, the suction device creates a negative (suction) pressure that draws fluid/air out of the working channel and out of an outlet opening provided in the suction valve. When the operator releases the suction valve (e.g. by not depressing the button anymore), the valve returns to its valve closed position that prohibits fluid/air flow and ends the suctioning out of the working channel. Often, the suction valve is removable from the endoscope/an endoscope handle so that potential blockage of the valve can be removed.

Basically, suction valves comprising a housing and a piston that is movable within the housing are well-known.

For example, U.S. Pat. No. 5,871,441 A discloses a suction valve that can be connected to a working channel of an endoscope and includes a (cylindrical) housing, a piston, a spring and a button. The piston is provided with a flow channel and is movably accommodated within the housing. The button (on top of the piston) is connected to the piston such that the piston is movable together with the button. An operator can press the button to move the piston from a valve closed state to a valve open state. The spring ensures that the valve is usually in the valve closed state, in particular when the operator does not press down the button. The housing is provided with an inlet opening that is connected to the working channel of the endoscope and with an outlet opening that is connected to a suction device. Usually, the suction device is active/running. When the valve is in the valve closed state an outer circumferential surface of the cylindrically shaped piston blocks the inlet opening. When the operator presses down the button, the piston is moved downwards such that the flow channel of the piston connects the inlet opening of the housing with the outlet opening of the housing, and a fluid flow through the suction valve is enabled. Hence, fluid/air can be drawn from the working channel of the endoscope through the suction valve.

U.S. Pat. No. 5,840,015 A discloses a suction valve that is assembled in a similar way as the suction valve disclosed in U.S. Pat. No. 5,871,441 A.

Usually, for reusable endoscopes suction valves are used that generally comprise metal parts. Metal parts can be manufactured with high precision and the valves can include proper sealings that ensure a good performance of the suction valves. However, for single use endoscopes/disposable endoscopes this solution is too expensive and resource-demanding. For single use endoscopes it is thus preferable to provide a suction valve which is essentially produced/manufactured of plastic/polymer/synthetic material. Plastic parts however cannot be produced as accurately as metal parts. In particular, for plastic parts tolerances are bigger than for metal parts. Furthermore, surfaces of molded plastic parts are usually slightly tapered (in order to allow removal of a mold/a mold core) which leads to challenges ensuring a proper sealing of the valve.

One such challenge is to prevent undesired suction of air from the surroundings of the suction valve, when the valve is in the valve open state. In particular, a suction effect of the suction device on the working channel shall not be decreased due to undesired suction of air from the surroundings. Hence, in the valve open state, the suction valve needs a proper sealing at least between the button and the housing.

For this purpose, e.g. US 2017/0290495 A1 discloses a suction valve which is operable in a way similar as the ones described in U.S. Pat. No. 5,871,441 A and in U.S. Pat. No. 5,840,015 A. Here, a button connected to a piston is provided, wherein the button and the piston are movable within the housing of the suction valve. The button is provided with a sealing element formed separately from the button. The sealing element is of an elastic material with self-adhesiveness to the button. When the button is pressed down by a user, the suction valve is transferred from the valve closed state to the valve open state. In the valve open state the separate sealing element contacts the upper/top rim of the housing and hence seals the suction valve against undesired suction of air from the surroundings.

A major drawback of a suction valve designed as described above is that the assembly of the suction valve can be challenging, as the individual components of the suction valve are small.

SUMMARY OF THE DISCLOSURE

The tasks and objectives of the present disclosure are to eliminate or at least to reduce the disadvantages of the prior art. In particular, a suction valve shall be provided which prevents an undesired suction of air from the surroundings in the valve open state and is thus appropriately sealed. Moreover, there is a need to simplify/ease an assembly of the suction valve. Further, integration of additional functions into the suction valve would be desirable.

The tasks and objectives are solved by an endoscope and a system in accordance with the claims. Advantageous embodiments are claimed in the dependent claims and/or are explained below.

The present disclosure relates to an endoscope, preferably a single use endoscope, that comprises a proximal endoscope handle, a distal tip unit configured to be inserted into a patient's body cavity, an endoscope shaft connecting the endoscope handle and the distal tip unit, a working channel provided in the endoscope shaft and extending from the endoscope handle towards the distal tip unit and a suction valve configured to control a suction through the working channel and having a valve closed state and a valve open state. The suction valve comprises: a housing having an inlet opening connected to the working channel and an outlet opening; and a piston unit inserted in the housing. The piston unit comprises a movable piston, a button attached to the piston, a fixation ring arranged stationary/immovable in the housing and a spring arranged and acting between the fixation ring and the button or piston. The button is a one-piece or integral part having an integrated sealing portion, the integrated sealing portion contacting the housing and providing a sealing between the button and the housing in the valve open state.

In other words, the endoscope according to the present disclosure has a suction valve comprising a button that is configured to provide an integrated sealing. The button is preferably already produced/manufactured with the integrated sealing and forms/constitutes one single piece/part. Hence, the sealing is integrated into the button and the button does not need to be provided with a separate sealing element/part in order to provide an appropriate sealing between the button and the housing in the valve open state. Therefore, the assembly process of the suction valve is eased as fewer components (no separate sealing element) have to be assembled.

In a preferred embodiment, the button comprises/consists of a first button portion made of a first material and a second button portion made of a second material, wherein the first material is different from the second material.

The first material may have a higher modulus of elasticity/elastic modulus than the second material. This means that the first material has preferably a higher stiffness/tensile strength than the second material. In other words, the first material is preferably more rigid than the second material or rather the second material is preferably more flexible than the first material.

Moreover, the first material and the second material may be both polymer materials. In this case, the button having the first and the second material is cheap to manufacture and thus appropriate for a single use endoscope. Especially preferred, the first material is a rigid polymer material (e.g. acrylonitrile-butadiene-styrene (ABS), polycarbonate (PC), etc.) and the second material is a flexible polymer material (e.g. thermoplastic polyurethane (TPE), silicone, etc.). According to the present disclosure, "rigid" and "flexible" shall preferably be understood in relation to a use situation, when a user applies ordinary pressure by his fingers. In particular, a "flexible" material is preferably a material, which deforms in this use situation, and a "rigid" material is preferably a material, which does not deform in this use situation.

It is preferable when the integrated sealing portion of the button is made of the second material. In other words, the second button portion preferably comprises the integrated sealing portion. It has turned out that when the integrated sealing portion is made of the second (flexible) material, it may adjust to the shape of any material more rigid. When the suction valve is transferred from the valve closed state to the valve open state, the integrated sealing portion is preferably brought into contact with the (rigid) housing, in particular an upper/top rim of the housing, and in this way adjusts to the shape of the housing/the top rim, thus providing an appropriate sealing between the button and the housing.

Preferably, the button is a multi-component injection molded part/is manufactured using a multi-component injection molding process. Especially preferred the button is a two-component injection molded part/is manufactured using a two-component injection molding process. In particular, a first component may be used to form the first button portion made of the first material and a second component may be used to form the second button portion made of the second material. It is conceivable that further components/further materials are used to form the button. In this way, a button being a one-piece or integral part having an integrated sealing portion can be easily manufactured.

According to a preferred embodiment, the second button portion (made of the second material) comprises the integrated sealing portion, an inner circular portion and an elongated portion, the elongated portion extending radially outwardly from the inner circular portion. When the second button portion not only comprises the integrated sealing portion, but also different other portions (i.e. when the function of the second button portion is not limited to the sealing between the button and the housing), additional functions can be integrated into the button.

Especially preferred, the inner circular portion and the elongated portion are visible from outside in an assembled state of the suction valve, and the integrated sealing portion is provided inside/on an inner side of the button and is not visible from outside in the assembled state of the suction valve. When portions of the second button portion can be seen from outside, these portions may serve as a visual marker or visual indication providing information, e.g. about the type of the valve or about an assembly of the valve, to a user.

In this context, it may be especially preferred when a color of the first material is different from a color of the second material. E.g. when the color of the second material is red and the color of the first material is different to red, it is clear for the user that the respective valve is a suction valve (as the color red is usually used to mark suction valves of endoscopes). It is to be understood that also other colors than red may be used for the second button portion made of the second material. As the second button portion is preferably visible from outside (in particular the inner circular portion and the elongated portion), the second button portion not only serves to provide an appropriate sealing between the button and the housing but also serves to provide information to a user.

In particular, the elongated portion of the second button portion may be used as a visual marker to show a user the correct orientation of the button relative to the housing when the piston unit is inserted into the housing or the correct orientation of the button relative to the piston when the button is attached to the piston.

In this context, it is especially preferred when only one elongated portion is provided extending radially outwardly from the inner circular portion.

Speaking more generally, the button preferably comprises a visual marker or a visual indication. Such a visual marker can help to orientate the button/the piston unit relative to the piston/the housing. The housing or the piston may be provided with a corresponding visual marker. Moreover, the visual marker or indication may provide information about a type of the valve (in this case that the valve is a suction valve) to a user/assembler of the valve.

The visual marker or the visual indication is preferably a colored portion of the button visible from outside in the assembled state of the suction valve.

In other words, it is advantageous when the button has colored external surfaces/a colored external surface.

The integrated sealing portion may have an essentially cylindrical shape (or an L-shape when the connection portion/area to the other portions, i.e. the inner circular portion and the elongated portion, of the second button portion is considered to be part of the integrated sealing portion) and may provide a sealing surface at an end thereof. This sealing surface may form the sealing with the housing in the valve open state.

The button may be alternatively described as comprising a round button cover portion and a cylindrical button shell portion extending from the button cover portion.

The round button cover portion may comprise the/an inner circular portion made of the second material and the/an outer circular portion made of the first material. Moreover, the round cover portion may comprises the/an elongated portion made of the second material and extending radially outwardly from the inner circular portion, the elongated portion thus interrupting the outer circular portion made of the first material. The inner circular portion and the elongated portion may have a different color compared to the outer circular portion. In this way, the elongated portion and the inner circular portion are easily visible for a user and can be used as a visual marker or a visual indication.

Summarized, when describing the button in this way, it may be preferred when the button cover portion comprises an outer circular portion, an inner circular portion and an elongated portion, the elongated portion extending radially outwardly from the inner circular portion and thus interrupting the outer circular portion, wherein the outer circular portion is made of a first material, the inner circular portion and the elongated portion are made of a second material, and a color of the first material is different from a color of the second material.

The button may be provided with at least one slit, preferably several slits, allowing leakage flow in the valve closed state. A leakage flow is the drawing in of surrounding air through slit(s) in the button. By providing the button with such slit(s), surrounding air may be suctioned through the suction valve in the valve closed state and hence an undesired residual suction through the working channel and through the inlet opening of the housing can be reduced or even eliminated. Leakage flow further reduces or even eliminates the risk of excessive initial suction when opening the valve.

The slit(s) are preferably provided in the cylindrical button shell portion. In this case, the slits are suitably placed to allow a leakage flow from the surroundings through the suction valve in the valve closed state. The slit(s) may have an elongated slotted hole shape. Especially preferred, a plurality of circumferentially (equidistantly) spaced apart slits are provided in the cylindrical button shell portion.

The housing may be formed essentially cylindrically. Moreover, the housing may have a cylindrically shaped receptacle for reception of the piston unit. The integrated sealing portion may contact a ring-shaped/annular rim of the housing in the valve open state.

The button may be configured to snap onto the piston. In particular, the button may have in inwardly protruding portion, the inwardly protruding portion protruding inwardly from the button cover portion and being configured to snap onto the piston. In this way, the piston can be easily coupled with the button and can hence be moved together with the button. The inwardly protruding portion is preferably made of the first material.

Moreover, the button may be configured to make a form-fit/snap connection with the housing at least in the valve closed state. In this way, the button may be configured to limit a movement of the piston when the spring urges the button or the piston into the valve closed state. In such way, the button does not part from the housing unintentionally.

Further, the suction valve may be configured to manually control the suction through the working channel. In particular, the suction valve can be transferred from the valve closed state to the valve open state by pressing the button towards the housing by a user. In this way, a user can easily control the suction valve and can switch from the valve closed state to the valve open state.

Preferably, the spring is configured to urge the suction valve into the valve closed state when no external force, e.g. a pressing force, acts on the button. Hence, when no external force acts on the button, the suction valve is in the valve closed state.

Furthermore, the suction valve or at least the piston unit of the suction valve is preferably configured to be removably attachable to the endoscope, in particular to the endoscope handle. In such way, when the suction valve or the piston unit can be easily removed from the endoscope/the endoscope handle, the suction valve/the piston unit can be easily cleaned.

In a further preferred embodiment of the suction valve, the inlet opening is connected to the working channel of the endoscope via a suction tube. In this way, an optimal coupling between the suction valve and the working channel of the endoscope can be ensured. Moreover, the suction tube ensures to minimize suction losses between (the inlet opening of) the suction valve and the working channel of the endoscope. There may also be a biopsy connector having a biopsy valve be arranged between the suction tube and the working channel. Anyway, it is preferred if there is not a direct connection between the inlet opening and the working channel.

Furthermore, the present disclosure relates to a system comprising the endoscope described before wherein the system further comprises a suction device that is connectable to the outlet opening.

The system may further comprise a monitor for showing an image captured by an image capturing means arranged at the distal tip unit.

BRIEF DESCRIPTION OF FIGURES

The disclosure is explained in more detail below using preferred embodiments and referring to the accompanying figures.

The figures are schematic in nature and serve only to understand the disclosure. Identical elements are marked with the same reference signs. The features of the different embodiments can be interchanged among each other.

DETAILED DESCRIPTION OF SELECTED EMBODIMENTS

Figure 1:
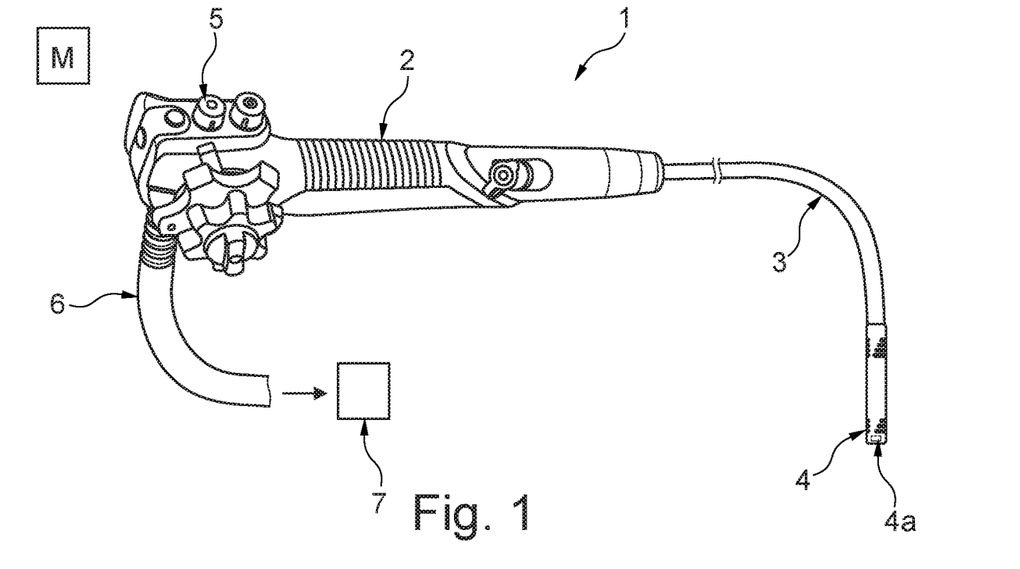
FIG. 1 is a perspective view of an endoscope comprising a suction valve.

In FIG. 1, an endoscope 1 is shown. The endoscope 1 is preferably configured as a single use endoscope and comprises a handle 2 designed to be held by a user. An at least partially flexible endoscope shaft 3 extends from the handle 2 to a distal tip unit 4, which is intended to be inserted into a patient's body cavity. The endoscope shaft 3 is (internally) provided with a working channel (not visible in the figures).

At the distal tip unit 4, image capturing means 4a, such as a miniature video camera, and illuminating means, such as light-emitting diodes or fibre optic light guides connected to a proximal source of light, are arranged/installed, such that the patient's body cavity can be illuminated and inspected. An image captured by the image capturing means can be shown on a monitor M. The monitor M is provided separately from and connected with the endoscope 1, wirelessly or by a cable extending from the handle. Further, the endoscope 1 is provided with the internal working channel 11a (shown in FIG. 4) which is formed within the endoscope shaft 3 and which may be configured to guide a surgical instrument from the proximal endoscope handle 2 into the patient's body cavity or to suction fluids via an opening at the distal tip unit. The user is therefore able to perform endoscopic examinations within the patient's body cavity.

A suction valve 5 is provided at the handle 2. Here, the suction valve 5 is inserted into the handle 2. One end of a suction tube 6 is connected to the suction valve 5. The other end of the suction tube 6 is connected to a suction device (a suction pump/vacuum pump) 7 that exerts a suction effect on the working channel 11a via the suction valve 5.

Figure 2:
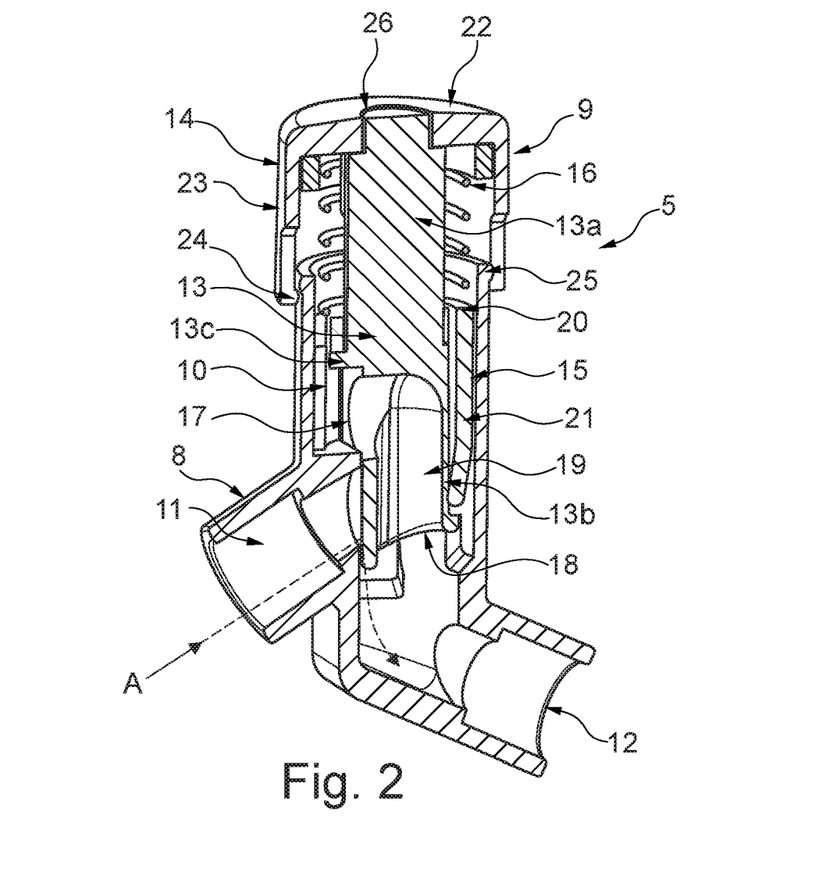
FIG. 2 is a longitudinal sectional view of a suction valve in a valve closed state.

FIG. 2 shows a longitudinal sectional view of a suction valve 5 according to a first preferred embodiment. The suction valve 5 comprises a housing 8 and a piston unit 9. In FIG. 2, the piston unit 9 is illustrated in a case in which it is accommodated in/inserted into the housing 8. The housing 8 is essentially formed as a hollow cylinder whose cavity defines an internal guiding channel 10. The piston unit 9 is inserted into an open (upper) end of the housing 8. An outer shell surface of the housing 8 is interrupted by a first protruding pipe portion which is angled, especially in an obtuse angle, relative to a length axis of the housing 8. The first protruding pipe portion defines the inlet opening 11 of the housing 8. The outer shell surface of the housing 8 is further interrupted by a second protruding pipe portion which is angled, especially in an obtuse angle, relative to the length axis of the housing 8. The first protruding pipe portion and the second protruding pipe portion are essentially diametrically opposed to each other and the first protruding pipe portion is arranged above the second protruding pipe portion in a length/axial direction of the housing 8. The second protruding pipe portion defines the outlet opening 12 of the housing 8.

The piston unit 9 accommodated in the internal guiding channel 10 comprises a piston 13, a button 14 that is fixed to the piston 13, a fixation ring 15 that is arranged immovably/stationary inside the housing 8 and a spring 16 that is positioned between the button 14 and the fixation ring 15. Although the spring 16 is positioned between the button 14 and the fixation ring 15 according to FIG. 2 it is to be understood that the spring 16 may alternatively be arranged and act between the piston 13 and the fixation ring 15 or between the button or pistion and the rim at the upper end of the housing. In other words, it is only necessary that the spring 16 biases the valve to the valve closed state. The spring 16 can thus be arranged and act between the assembly consisting of the piston 13 and the button 14, and the fixation ring 15 or the housing 8. The internal guiding channel 10 is configured to accommodate the piston unit 9 such that the piston 13 is movable/slidable inside the internal guiding channel 10.

The piston 13 includes a cylindrically shaped first (upper) piston portion 13a and a second (lower) piston portion 13b both merging into a transition area 13c arranged between the first piston portion 13a and the second piston portion 13b. The first piston portion 13a, the second piston portion 13b and the transition area 13c are integrally connected with each other.

The transition area 13c is provided with a radially outwardly protruding rim portion that is arranged between the first piston portion 13a and the second piston portion 13b. The radially outwardly protruding rim portion is urged against the fixation ring 15 by the spring 16 in the valve closed state. Alternatively or additionally, the transition area could comprise a slot and the fixation ring 15 could include a radially inward protrusion translating in the slot as the piston translates axially, the end of the slot urged against the radially inward protrusion to stop upward movement of the piston in the valve closed state.

The second piston portion 13b is provided with a cavity that interrupts a shell surface of the second piston portion 13b defining a first (side) opening 17 of the piston 13 and that interrupts a free end surface (bottom side) of the second piston portion 13b defining a second (bottom) opening 18 of the piston 13. The cavity between the first opening 17 and the second opening 18 defines a flow channel 19 of the piston 13 that allows a fluid flow between the first opening 17 and the second opening 18. The second opening 18 of the piston 13 is in fluid connection with the outlet opening 12 of the housing 8.

The fixation ring 15 comprises a ring-shaped/annular/circular ring-like portion 20 (afterwards simply called "ring-shaped portion 20") from which a protruding portion 21 is extending. The protruding portion 21 contacts the second piston portion 13b. The ring-shaped portion 20 encircles/encloses/surrounds the first piston portion 13a. The piston 13 is movable relative to the ring-shaped portion 20 of the fixation ring 15. When the piston unit 9 is accommodated within the housing 8, the fixation ring 15 is preferably fixed within/to the housing 8.

The protruding portion 21 of the fixation ring 15 is designed as a spring-type finger in FIG. 2, and urges/presses the piston 13, in particular the second piston portion 13b towards the inlet opening 11 by a spring force. This spring-type finger is configured as a leaf spring. In particular, the protruding portion 21 has a first (upper) portion extending essentially in an axial direction of the suction valve (along the piston 13) and a second (lower) portion being inclined with respect to the first (upper) portion towards the piston 13 (towards the second piston portion 13b) and contacting/pressing onto the piston 13 with a free end of the protruding portion 21.

The button 14 encompasses and covers the open end of the housing 8. For this purpose, the button 14 is formed like a hollow cylinder. The button 14 has a round button cover portion 22 and a cylindrical button shell portion 23 extending from the button cover portion 22. The button 14 is open at a free end that is opposed to the button cover portion 22. Hence, the button 14 defines an internal button cavity that is configured to accommodate the housing 8. The button 14 and the housing 8 are connectable with each other in a snap fit engaging manner. For this purpose, the open end of the button 14 is provided with an inwardly extending first snap-fit rim 24 and the (upper) end of the housing 8 that may be brought in contact with the button 14 is provided with an outwardly extending second snap-fit rim 25. When the piston unit 9 is connected to the housing 8, the first and the second snap-fit rims 24, 25 work together in such way that they limit a longitudinal movement of the piston 13 (unit) relative to the housing 8.

At its center, the button cover portion 22 is provided with a circular hole 26 of such a size that it can accommodate the free (upper) end of the first piston portion 13a. In this way, the button 14 is fixable to the piston 13 such that the piston 13 is movable together with the button 14.

The spring 16 is interposed between the ring-shaped portion 20 of the fixation ring 15 and the button 14. In FIG. 2, one end of the spring 16 contacts the ring-shaped portion 20 and the other end of the spring 16 contacts an inner surface of the button cover portion 22. The elastic force of the spring 16 is at least so large that the piston 13 is held in such a position relative to the housing 8 that a shell surface of the second piston portion 13b covers/seals the inlet opening 11 of the housing 8 in the valve closed state, as can be seen in FIG. 2. Hence, FIG. 2 shows a valve closed state, in which the piston 13 seals the inlet opening 11 against a fluid flow through the suction valve 5.

In FIG. 2, arrow A indicates a residual suction that enters the suction valve over the inlet opening in the valve closed state. This residual suction occurs when the suction device is running in the valve closed state and the inlet opening is not completely sealed by the second piston portion 13b. The object of the present disclosure is to reduce the residual suction as much as possible or to even eliminate the residual suction.

Figure 3:
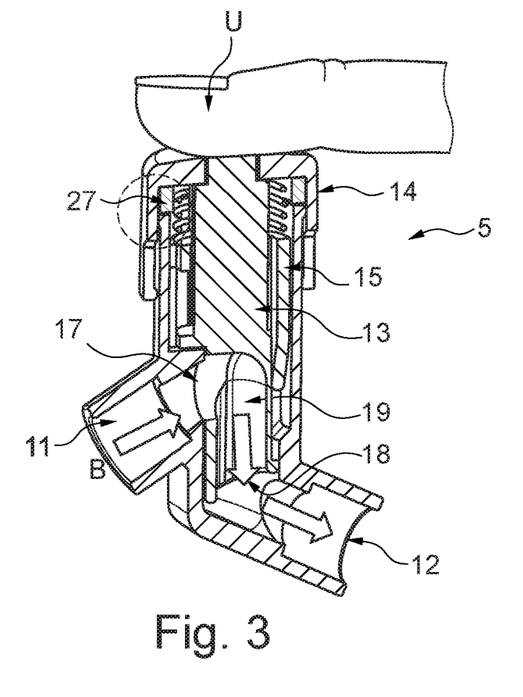
FIG. 3 is a longitudinal sectional view of the suction valve of FIG. 2 in a valve open state.

FIG. 3 shows a longitudinal sectional view of the suction valve 5 of FIG. 2 in the valve open state. In this case, the inlet opening 11 is in direct contact/is flush with the first opening 17 such that a fluid flow, indicated by an arrow B, from the inlet opening 11 through the flow channel 19 of the piston 13 and to the outlet opening 12 is allowed. Hence, in the valve open state, fluid, like air, water or mucus, from the patient's body cavity can be suctioned/drawn out of the working channel by the suction device 7. This improves the sight and hence the working accuracy of a user of the endoscope.

Advantageously, the inlet opening 11 and the first opening 17 have the same diameter (at least where the inlet opening 11 and the first opening 17 are in flush contact) to prohibit fluid losses in the valve open state.

The suction valve 5 can be transitioned from the valve closed state to the valve open state in the following way:

First, a user, indicated by U, can manually press (with his finger) the button 14 towards the housing 8 (pressing force acting in a length direction of the suction valve 5). The pressing force of the user U must at least be so great that the elastic force of the spring 16 is overcome, in order to compress the spring 16. Associated with this, the button 14 moves (downwards) together with the piston 13. In this way, the piston 13 is moved/slided downwards inside the internal guiding channel 10 of the housing 8 until the outwardly protruding rim portion in the transition area 13c of the piston 13 contacts a stop provided inside the housing 8/the internal guiding channel 10. In this valve open state the first opening 17 and the inlet opening 11 are in flush contact with each other. Moreover, a sealing element 27 provided on an inner side of the button cover portion 22 contacts the (upper) free end of the housing 8. In the valve open state, the sealing element 27 seals the suction valve 5 against suctioning/drawing in air from the surroundings. The sealing element 27 is a separate part which may be fixed/attached, e.g. bonded/glued to the inner side of the button cover portion 22.

When the suction valve 5 shall again be transferred from the valve open state to the valve closed state, the user U simply has to stop pressing onto the button 14 (e.g. by simply releasing his finger). In this case, the spring 16 relaxes and its elastic force moves the button 14 and the piston 13 in a direction away from the housing 8 (outwardly) back into the valve closed state.

Figure 4:
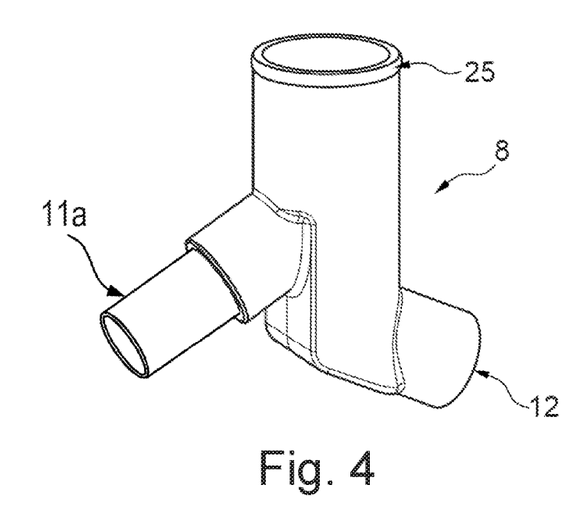
FIG. 4 is a perspective view of a housing.

FIG. 4 is a perspective view of the housing 8. Here, the shape of the housing 8 can be seen in detail. The housing 8 is formed essentially like a hollow cylinder. The (upper) end of the housing 8 that can be brought in contact with the button 14 is open and round/circular and defines the second snap-fit rim 25. The housing 8 has in total three openings. In addition to the opening at the upper end there is provided the inlet opening 11 and the outlet opening 12. Both the inlet opening 11 and the outlet opening 12 are formed as protruding pipe portions. The opening 11 can receive or be connected to a working channel 11a.

Figure 5:
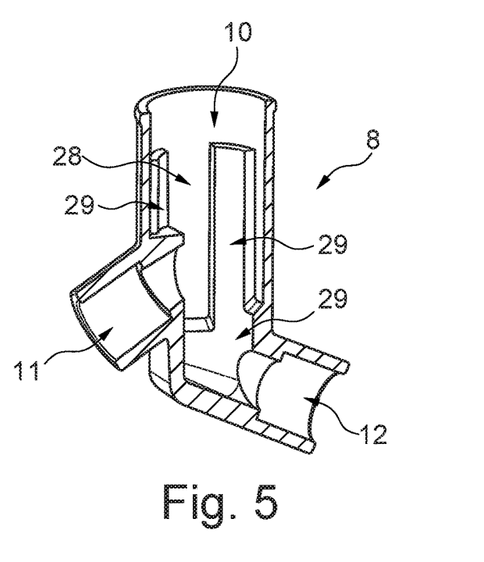
FIG. 5 is a longitudinal sectional view of the housing.

FIG. 5 is a longitudinal section view of the housing 8. Here, the formation of the internal guiding channel 10 can be seen in detail. The internal guiding channel 10 is provided with at least one groove 28 that extends in a length direction of the housing 8 along its inner surface. The at least one groove 28 is formed by adjacent protruding guiding portions 29 protruding inwardly from an internal wall of the housing 8. The groove 28 allows a leakage flow through the suction valve 5, especially through the internal guiding channel 10 and the flow channel 19, in the valve closed state.

Figure 6:
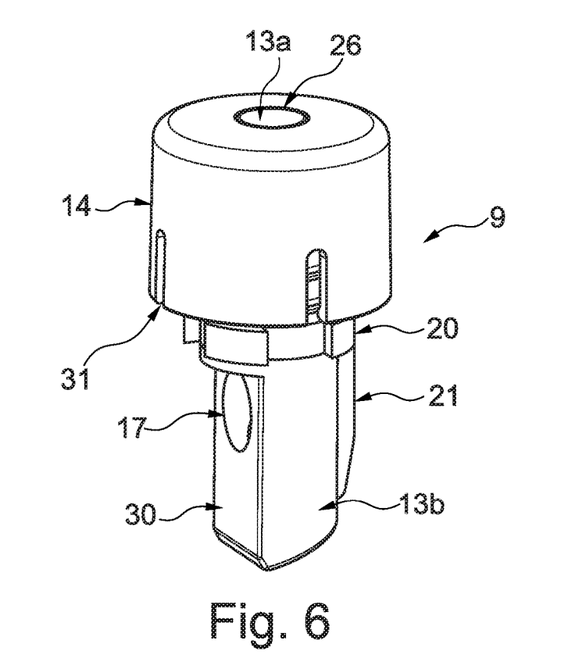
FIG. 6 is a perspective view of a piston unit.

FIG. 6 is a perspective view of the piston unit 9. It can be seen that the second piston portion 13b of the piston 13 is a cylinder whose shell surface is interrupted by a planar surface 30 that extends in a length direction of the piston 13. The planar surface 30 is configured to contact the inlet opening 11 of the housing 8 and is provided with the first opening 17 which is flush with the inlet opening 11 in the valve open state. Preferably, the internal guiding surface 10 (the inner shell surface of the housing 8) is provided with a correspondingly flat surface at a position/an area around/adjacent the inlet opening 11.

Moreover, it can be seen from FIG. 6, that the outer shell surface of the ring-shaped portion 20 of the fixation ring 15 is not continuous but interrupted by a plurality of (equidistantly separated) recesses. These recesses are configured to accommodate the protruding guiding portions 29 of the internal guiding channel 10. The protruding guiding portions 29 fit into the recesses of the ring-shaped portion 20 such that the fixation ring 15 can be fixed to the housing 8.

Furthermore, it can be seen from FIG. 6, that the cylindrical button shell portion 23 is provided with at least one, here with a plurality of (circumferentially equidistantly arranged) leakage slits 31 extending lengthwise from the open end of the button 14. The leakage slits 31 have an elongated slotted hole shape and allow air from the surroundings to be sucked into the suction valve 5 in the valve closed state. When the suction device 7 is running in the valve closed state, a leakage flow of air through the internal guiding channel 10 and through the flow channel 19 is basically desired. This has the purpose of avoiding a built-up of a vacuum in the valve closed state which would result in an undesirable rapid increase in suction flow when the suction valve 5 is transferred from the valve closed state to the valve open state. A rapid increase in suction flow could lead to damages to the tissue of the patient's body cavity. Typically, a slower increase in suction flow is desired when the suction device 5 is transferred to the valve open state. With the leakage flow entering the suction valve 5 over the leakage slits 31 the pressure in the suction valve 5 is closer to the atmospheric pressure and therefore the (residual) suction in the valve closed state can be reduced.

Figure 7:
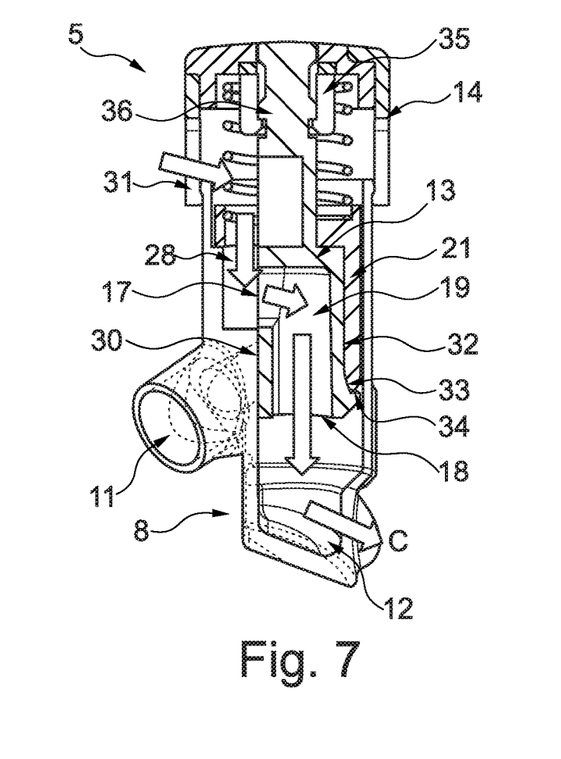
FIG. 7 is a longitudinal sectional view of a suction valve in a valve closed state indicating a leakage flow.

FIG. 7 is a longitudinal sectional view of a suction valve 5 according to a second preferred embodiment in the valve closed state. In FIG. 7 a leakage flow entering over the leakage slits 31 into the button 14 is indicated by means of arrow C. Here, it can be seen that the leakage flow first flows along the groove 28 of the internal guiding channel 10 and then enters the flow channel 19 of the piston 13 via the first opening 17. The leakage flow exits the piston 13 via the second opening 18 and then exits the suction valve 5 via the outlet opening 12.

As already described above, in the valve closed state, the piston 13, especially the planar surface 30 of the piston 13 contacting the correspondingly flat surface of the internal guiding channel 10, seals the inlet opening 11. It is an aim of this disclosure that the residual suction entering the suction valve 5 over the inlet opening 11 shall be reduced or even eliminated in the valve closed state. For this purpose an effective sealing between (the planar surface 30 of) the piston 13 and the inlet opening 11 is necessary. Against this background, in this disclosure, the fixation ring 15 is configured to urge the piston 13 against the inlet opening 11. FIG. 7 shows a second embodiment that allows the fixation ring 15 to exert an urging effect on the piston 13.

FIG. 7 shows a piston 13 of the suction valve 5 wherein the second piston portion 13b has an axially extending shell portion 32 (afterwards simply called "shell portion") and an inclined portion 33 integrally connected to/formed at an end of the shell portion 32. The inclined portion 33 is at such position that the protruding portion 21 of the fixation ring 15 can contact this inclined portion 33 such as to apply a pressing force onto the piston 13 towards the inlet opening 11. In the inclined portion 33 an outer diameter of the piston 13 gradually/continuously/linearly increases (starting) from the shell portion 32. The protruding portion 21 of the fixation ring 15 is formed like a wedge and engages at least with the inclined portion 33 in the valve closed state, thus urging the inclined portion 33 towards the inlet opening 11 of the housing 8.

In this case, the second piston portion 13b is not just provided with an inclined portion 33 to allow the urging effect, but the end of the second piston portion 13b is further provided with a radially outwardly protruding flange portion 34 (afterwards simply called "flange portion"). The inclined portion 33 is arranged between the shell portion 32 and the flange portion 34. The inclined portion 33 and the flange portion 34 form together a holding portion. This holding portion can engage with the wedge-like protruding portion 21 of the fixation ring 15. The flange portion 34 may accommodate the wedge-like protruding portion 21 of the fixation ring 15. In the valve closed state, the wedge-like protruding portion 21 contacts the inclined portion 33 and may be held by the flange portion 34. As the inclined portion 33 extends outwardly starting from the shell portion 32, in the valve-closed state, the wedge-like protruding portion 21 of the fixation ring 15 exerts a pressing force onto the inclined portion 33 which is directed towards the inlet opening 11. Hence, the piston 13 is urged/pressed by (the wedge-like protruding portion 21 of) the fixation ring 15 against the inlet opening 11 and hence effectively seals the inlet opening 11 against an undesired residual suction. Thus, in the valve closed state, only a desired leakage flow C entering over the leakage slits 31 streams through the suction valve 5.

As already described above, at least two embodiments are imaginable to enable an urging effect of the fixation ring 15 onto the piston 13 towards the inlet opening 11. The first embodiment is that the protruding portion 21 of the fixation ring 15 is designed as a spring-type finger, urging the piston 13 towards the inlet opening by a spring force, as can be seen in FIG. 2 and FIG. 3.

Moreover, in the embodiment shown in FIG. 7 (as well as in FIG. 8), a special fixing mechanism between the button 14 and the piston 13 is visible. Here, the button 14 has a first holding arrangement 35 which comprises an inwardly protruding portion, the inwardly protruding portion protruding inwardly from the button cover portion 22 and being configured to snap onto the piston 13. The first piston portion 13a is provided with a second holding arrangement 36. The second holding arrangement 36 of the piston 13 is configured to be complementary to and to be engaged with the first holding arrangement 35 of the button 14. The interaction of the first and second holding arrangements 35, 36 allows a snap-fit arrangement between the button 14 and the piston 13.

Figure 8:
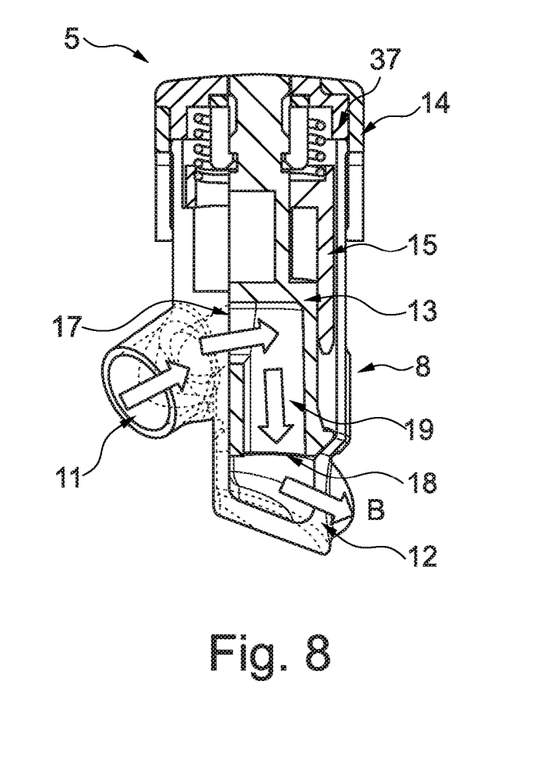
FIG. 8 is a longitudinal sectional view of the suction valve of FIG. 7 in a valve open state indicating a suction flow.

FIG. 8 is a longitudinal sectional view of the suction valve 5 of FIG. 7 in the valve open state. Here, due to the valve open state, a fluid/suction flow, indicated by arrow B, between the inlet opening 11 and the outlet opening 12 is allowed. Compared to FIG. 7, the button 14 was pushed (downwards) towards the housing 8 such that the piston 13 is in such height that its first opening 17 is in flush contact with the inlet opening 11 of the housing 8. Furthermore, it can be seen that the fixation ring 15 has the same position in the valve open state as in the valve closed state as (the ring-shaped portion 20 of) the fixation ring 15 is fixed to the housing 8. Therefore, in the valve open state the wedge-like protruding portion 21 of the fixation ring 15 is not in contact with the inclined portion 33 of the piston 13 and thus does not urge the piston 13 towards the inlet opening 11.

In the second embodiment shown in FIG. 7 and FIG. 8 a special preferred embodiment of the button 14 is realized. It is to be understood however that this special preferred embodiment of the button may also be applied for the first embodiment shown in FIG. 2 and FIG. 3. In other words the configuration of the button 14 in the second embodiment shown in FIG. 7 and FIG. 8 may also be applied for the first embodiment shown in FIG. 2 and FIG. 3.

As already discussed above, in the first embodiment shown in FIG. 2 and FIG. 3 a separate sealing element 27 is attached to the inner side of the button cover portion 22. According to a special preferred embodiment the button 14 may however be integrally provided with a sealing. In particular the button 14 may be a one-piece or integral part having an integrated sealing portion 37 replacing the separate sealing element 27. As can be seen in particular in FIG. 8 the integrated sealing portion 37 contacts the (upper free end of the) housing 8 and provides a sealing between the button 14 and the housing 8 in the valve open state. The integrated sealing portion 37 seals the suction valve 5 in the valve open state against undesired suction of air from the surroundings.

Figure 9:
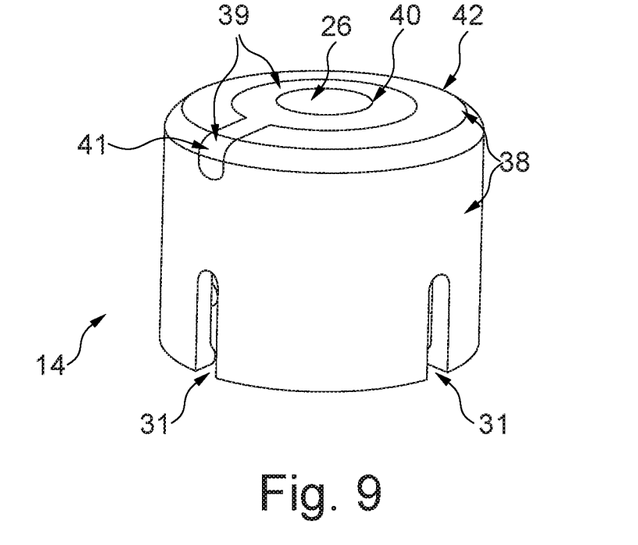
FIG. 9 is a perspective view of a preferred embodiment of a button comprising a first button portion and a second button portion.

FIG. 9 is a perspective view of the button 14 according to the special preferred embodiment. As can be seen, the button 14 comprises a first button portion 38 and a second button portion 39. Preferably, the first button portion 38 is made of a first material and the second button portion 39 is made of a second material. The first material may have a higher modulus of elasticity than the second material (the first material is more rigid than the second material).

The second button portion 39 (made of the second material) comprises the integrated sealing portion 37, an inner circular portion 40 and an elongated portion 41. The inner circular portion 40 is at its center provided with the circular hole 26. The elongated portion 41 extends radially outwardly from the inner circular portion 40. The first button portion 38 is visually distinguishable from the second button portion 39. Preferably, the second button portion 39 is of another colour than the first button portion 38, especially the second button portion 39 is red as this colour indicates a user that this valve is used to control suction of the endoscope, whereas the first button portion 38 is of another colour than red. When the integrated sealing portion 37 is provided integrally with the button 14, no additional and/or separate sealing is necessary for such a suction valve 5. Hence, the assembly of such suction valve 5 can be simplified.

In FIG. 9, it can be seen, that the button cover portion 22 comprises the inner circular portion 40 made of the second material and an outer circular portion 42 made of the first material. Moreover, the button cover portion 22 comprises the elongated portion 41. The inner circular portion 40 is arranged at the center of the button cover portion 22 and is encircled by the outer circular portion 42 of the first material.

In FIG. 9, also one single elongated portion 41 can be seen. The elongated portion 41 is a portion that extends from the inner circular portion 40 in a radial direction of the button 14 towards an outer edge of the button 14 at which the button cover portion 22 merges into the outer cylindrical button shell portion 23. The elongated portion 41 can be used as a marking/a visual marker to show a user the correct orientation of the button 14 relative to the housing 8 or relative to the piston 13, when mounting the piston unit 9 to the housing 8 or when mounting the button 14 to the piston 13. For this purpose, the housing 8 or the piston 13 may have a corresponding marking, which is not shown in the figures. In this way, the button 14 indicates the correct orientation of the button 14 to an assembler/user.

By providing the integrated sealing portion 37 in the button 14, the assembly process is eased as fewer components need to be handled. By providing a visual marker on the external surface of the button 14, the assembly process is eased as the assembler can readily infer the correct orientation of the button 14 for assembly with the remaining components of the valve. By providing a coloured external surface, the use of the button 14 is improved since the user can easily determine the function of the (suction) valve 5 as the red colour is commonly used to indicate a suction function.

Figure 10:
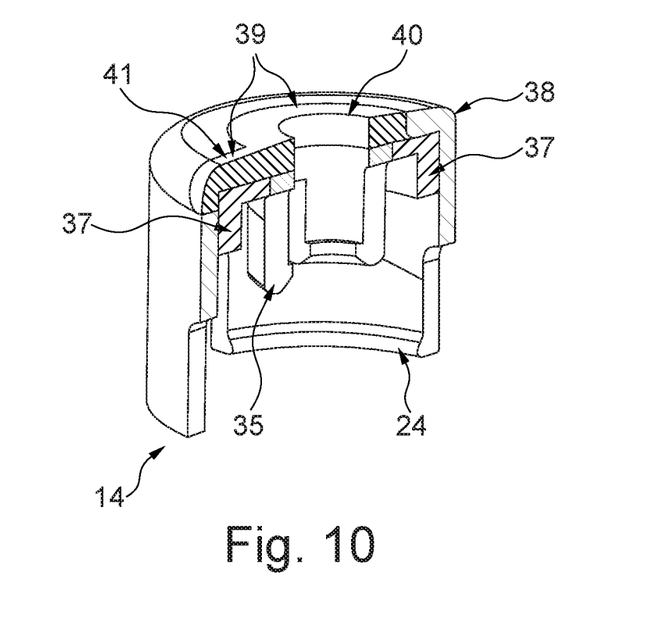
FIG. 10 is a longitudinal sectional view of the button of FIG. 9 comprising the first button portion and the second button portion.

In FIG. 10, a longitudinal sectional view of the button 14 according to the special embodiment can be seen. Here, the second button portion 39 is completely visible. It is to be understood that although different hatchings are used for different portions (inner circular portion 40, elongated portion 41, sealing portion 37) of the second button portion 39 and for different portions of the first button portion 38 in FIG. 10, the second button portion 39 is an integral, one-material portion and the entire button is an integral, one-piece and multi-material part. The integrated sealing portion 37 is arranged inside of the button 14 (on an inner side) and has an L-shaped cross-section, wherein a first leg of the L extends in a radial direction of the button 14 and a second leg of the L extends in a longitudinal direction of the button 14. An end of the second leg provides a sealing surface and is in contact with the housing 8 (in particular with the annular upper rim of the housing 8) in the valve open state. In this way, the integrated sealing portion 37 seals the suction valve 5 against undesired suction of air from the surroundings in the valve open state.

Furthermore, it can be seen in FIG. 10 that according to the special embodiment of the button 14, the first holding arrangement 35 extends towards the housing 8 from an inner surface of the inner circular portion 40. The first holding arrangement 35 may be made of the first material.

The first and the second materials of the button 14 are preferably a first and a second (polymer) material. The first material may be a rigid polymer, e.g. acrylonitrile-butadiene-styrene (ABS) or polycarbonate (PC), which is used for the first button portion 38. The second material may be a flexible polymer able to form a sealing, such as thermoplastic polyurethane (TPU) or silicone, which is used for the second button portion 39. The button 14 may be manufactured using a multi (two)-component injection molding process.

The following items are examples of various embodiments disclosed above:

Item 1. An endoscope (1) comprising: a proximal endoscope handle (2); a distal tip unit (4) configured to be inserted into a patient's body cavity; an endoscope shaft (3) connecting the endoscope handle (2) and the distal tip unit (4); a working channel provided in the endoscope shaft (3) and extending from the endoscope handle (2) towards the distal tip unit (4); and a suction valve (5) configured to control a suction through the working channel and having a valve closed state and a valve open state; the suction valve (5) comprising: a housing (8) having an inlet opening (11) connected to the working channel and an outlet opening (12); and a piston unit (9) inserted in the housing (8), the piston unit (9) comprising: a movable piston (13); a button (14) attached to the piston (13); a fixation ring (15) arranged stationary in the housing (8); and a spring (16) arranged and acting between the fixation ring (15) and the button (14) or piston (13); the button (14) being a one-piece or integral part having an integrated sealing portion (37), the integrated sealing portion (37) contacting the housing (8) and providing a sealing between the button (14) and the housing (8) in the valve open state.

Item 2. Endoscope (1) according to item 1, wherein the button (14) comprises a first button portion (38) made of a first material and a second button portion (39) made of a second material, wherein the first material is different from the second material.

Item 3. Endoscope (1) according to item 2, wherein the first material and the second material are both polymer materials and the first material is a rigid polymer material and the second material is a flexible polymer material.

Item 4. Endoscope (1) according to item 2 or 3, wherein the second button portion (39) comprises the integrated sealing portion (37).

Item 5. Endoscope (1) according to any of items 2 to 4, wherein the second button portion (39) comprises the integrated sealing portion (37), an inner circular portion (40) and an elongated portion (41), the elongated portion (41) extending radially outwardly from the inner circular portion (40).

Item 6. Endoscope (1) according to item 5, wherein the inner circular portion (40) and the elongated portion (41) are visible from outside in an assembled state of the suction valve (5), and the integrated sealing portion (37) is provided on an inner side of the button (40) and is not visible from outside in the assembled state of the suction valve (5).

Item 7. Endoscope (1) according to any of items 2 to 6, wherein a color of the first material is different from a color of the second material.

Item 8. Endoscope (1) according to item 1, wherein the button (14) comprises a round button cover portion (22) and a cylindrical button shell portion (23) extending from the button cover portion (22).

Item 9. Endoscope (1) according to item 8, wherein the button cover portion (22) comprises an outer circular portion (42), an inner circular portion (40) and an elongated portion (41), the elongated portion (41) extending radially outwardly from the inner circular portion (40) and thus interrupting the outer circular portion (42), wherein the outer circular portion (42) is made of a first material, the inner circular portion (40) and the elongated portion (41) are made of a second material, and a color of the first material is different from a color of the second material.

Item 10. Endoscope (1) according to item 8 or 9, wherein the button (14) has an inwardly protruding portion (35), the inwardly protruding portion (35) protruding inwardly from the button cover portion (22) and being configured to snap onto the piston (13).

Item 11. Endoscope (1) according to any of items 8 to 10, wherein the button (14) is provided with at least one leakage slit (31), preferably several leakage slits, allowing leakage flow in the valve closed state, the at least one leakage slit (31) being provided in the cylindrical button shell portion (23).

Item 12. Endoscope (1) according to any of items 1 to 11, wherein the button (14) is a multi-component injection molded part.

Item 13. System comprising an endoscope (1) according to any of items 1 to 12, wherein the system further comprises a suction device (7) connectable to the outlet opening (12).

Item 14. System according to item 13, wherein the system further comprises a monitor (M) for showing an image captured by an image capturing means arranged at the distal tip unit (4).

I claim:

1. An endoscope comprising:
   a handle;
   an endoscope shaft extending from the handle, the endoscope shaft having a distal end;
   a working channel provided in the endoscope shaft and extending from the handle towards the distal end of the endoscope shaft; and
   a suction valve configured to control a suction through the working channel and having a valve closed state and a valve open state, the suction valve comprising:
   a housing having an upper end, an inlet opening and an outlet opening, the inlet opening connected to the working channel; and
   a piston unit inserted in the housing, the piston unit comprising:
   a movable piston;
   a spring surrounding the piston and biasing the valve to the valve closed state; and
   a one-piece part comprising a button and a sealing portion, the button attached to the piston and including a button cover portion and a shell portion extending longitudinally from the cover portion, the button defining an internal button cavity configured to accommodate the upper end of the housing, the shell portion including an upper end connected to the button cover portion and a lower end surrounding the upper end of the housing in the valve closed state, the lower end of the shell portion translating longitudinally over the upper end of the housing as the piston translates longitudinally to transition the suction valve from the valve closed state to the valve open state, and the sealing portion surrounding the piston and contacting the housing in the valve open state to provide a sealing between the button and the housing in the valve open state.

2. The endoscope of claim 1, wherein the button comprises a first button portion made of a first material and a second button portion made of a second material, wherein the first material is different from the second material.

3. The endoscope of claim 2, wherein the first material and the second material are both polymer materials and the first material is a rigid polymer material and the second material is a flexible polymer material.

4. The endoscope of claim 2, wherein the second button portion comprises the sealing portion.

5. The endoscope of claim 2, wherein the second button portion comprises the sealing portion, an inner circular portion and an elongated portion, the elongated portion extending radially outwardly from the inner circular portion.

6. The endoscope of claim 5, wherein the inner circular portion and the elongated portion are visible from outside the suction valve in an assembled state of the suction valve, and the sealing portion is provided on an inner side of the button and is not visible from the outside of the suction valve in the assembled state of the suction valve.

7. The endoscope of claim 2, wherein a color of the first material is different from a color of the second material.

8. The endoscope of claim 1, wherein the button cover portion comprises an outer circular portion, an inner circular portion and an elongated portion, the elongated portion extending radially outwardly from the inner circular portion and thus interrupting the outer circular portion, wherein the outer circular portion is made of a first material, the inner circular portion and the elongated portion are made of a second material, and a color of the first material is different from a color of the second material.

9. The endoscope of claim 1, wherein the button has an inwardly protruding portion, the inwardly protruding portion protruding inwardly from the button cover portion and being configured to snap onto the piston.

10. The endoscope of claim 9, wherein the shell portion comprises at least one leakage slit allowing leakage flow in the valve closed state.

11. The endoscope of claim 1, wherein the one-piece part is a multi-component injection molded part.

12. The endoscope of claim 1, wherein the housing comprises a cylindrical portion defining a guiding channel, the endoscope further comprising a fixation ring arranged to be stationary in the cylindrical portion of the housing, the fixation ring being axially aligned with and receiving the piston.

13. The endoscope of claim 12, wherein the cylindrical portion comprises a rim and the sealing portion contacts the rim of the housing in the valve open state.

14. The endoscope of claim 13, wherein the housing comprises a first protruding pipe portion defining the inlet opening and a second protruding pipe portion defining the outlet opening, wherein the piston comprises a flow channel, and wherein the flow channel establishes fluid communication between the inlet opening and the outlet opening in the valve open state.

15. The endoscope of claim 12, wherein the spring is arranged and acting between the fixation ring and the button or the piston.

16. A system comprising the endoscope of claim 1, wherein the endoscope comprises an image capturing means, and wherein the system further comprises a monitor operable to show an image captured by the image capturing means.

17. The system of claim 16, wherein the system further comprises a suction device operable to provide the suction at the outlet opening.

* * * * *